United States Patent [19]

Keith et al.

[11] Patent Number: 5,255,690
[45] Date of Patent: Oct. 26, 1993

[54] METHOD AND APPARATUS FOR PROXIMAL SUPPORT OF A GUIDE WIRE DURING CATHETER EXCHANGE

[75] Inventors: Peter T. Keith, Fridley; Thomas V. Ressemann, St. Cloud, both of Minn.

[73] Assignee: SciMed Life Systems, Inc., Maple Grove, Minn.

[21] Appl. No.: 914,873

[22] Filed: Jul. 16, 1992

[51] Int. Cl.[5] .................................................. A61B 5/00
[52] U.S. Cl. ..................................... 128/772; 604/96
[58] Field of Search .............. 128/657, 772; 604/93, 604/96, 158, 160, 164, 165, 171

[56] References Cited

U.S. PATENT DOCUMENTS

| | | | |
|---|---|---|---|
| 4,573,470 | 3/1986 | Samson et al. | 128/657 |
| 4,616,652 | 10/1986 | Simpson | 128/657 |
| 4,748,982 | 6/1988 | Horzewski et al. | 128/344 |
| 4,762,129 | 8/1988 | Bonzel | 128/344 |
| 4,824,435 | 4/1989 | Giesy et al. | 128/303 |
| 4,844,092 | 7/1989 | Rydell et al. | 128/772 |
| 5,040,548 | 8/1991 | Yock | 128/898 |
| 5,154,725 | 10/1992 | Leopold | 604/96 |

*Primary Examiner*—Max Hindenburg
*Attorney, Agent, or Firm*—Kinney & Lange

[57] ABSTRACT

A method and apparatus are provided for withdrawing a catheter proximally from a guide catheter lumen while supporting a guide wire in a longitudinal and lateral direction proximal to the guide catheter lumen. The guide catheter lumen has a guide catheter lumen, a proximal end and a distal end. A catheter extends through the guide catheter lumen and has a guide wire lumen at a distal portion thereof having a proximal end and a distal end. A length of the guide wire lumen is shorter than a length of the catheter. A guide wire extends through the guide wire lumen and the guide catheter lumen. A sleeve is provided over a segment of the guide wire extending proximally from the guide catheter lumen. The sleeve maintains that segment of the guide wire in close lateral proximity to the catheter as the catheter is withdrawn proximally from the guide catheter lumen and the guide wire is restrained from such proximal movement.

52 Claims, 8 Drawing Sheets

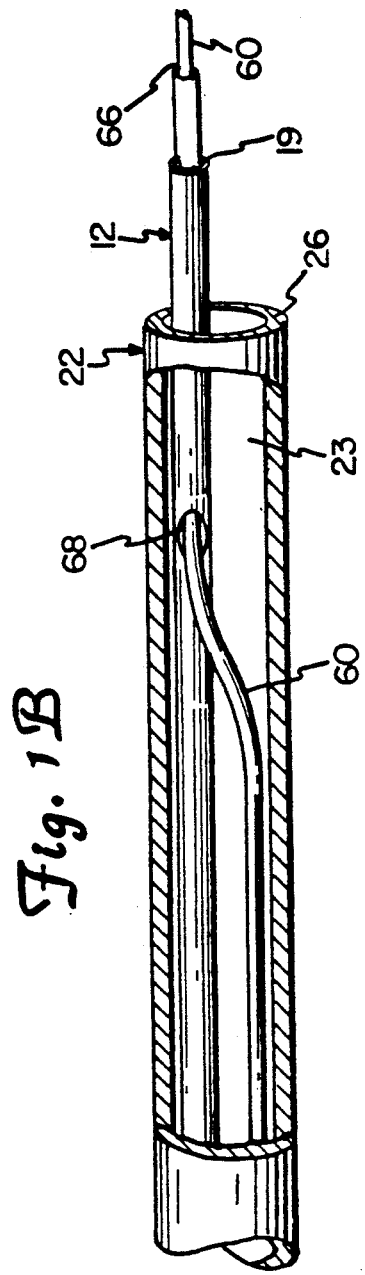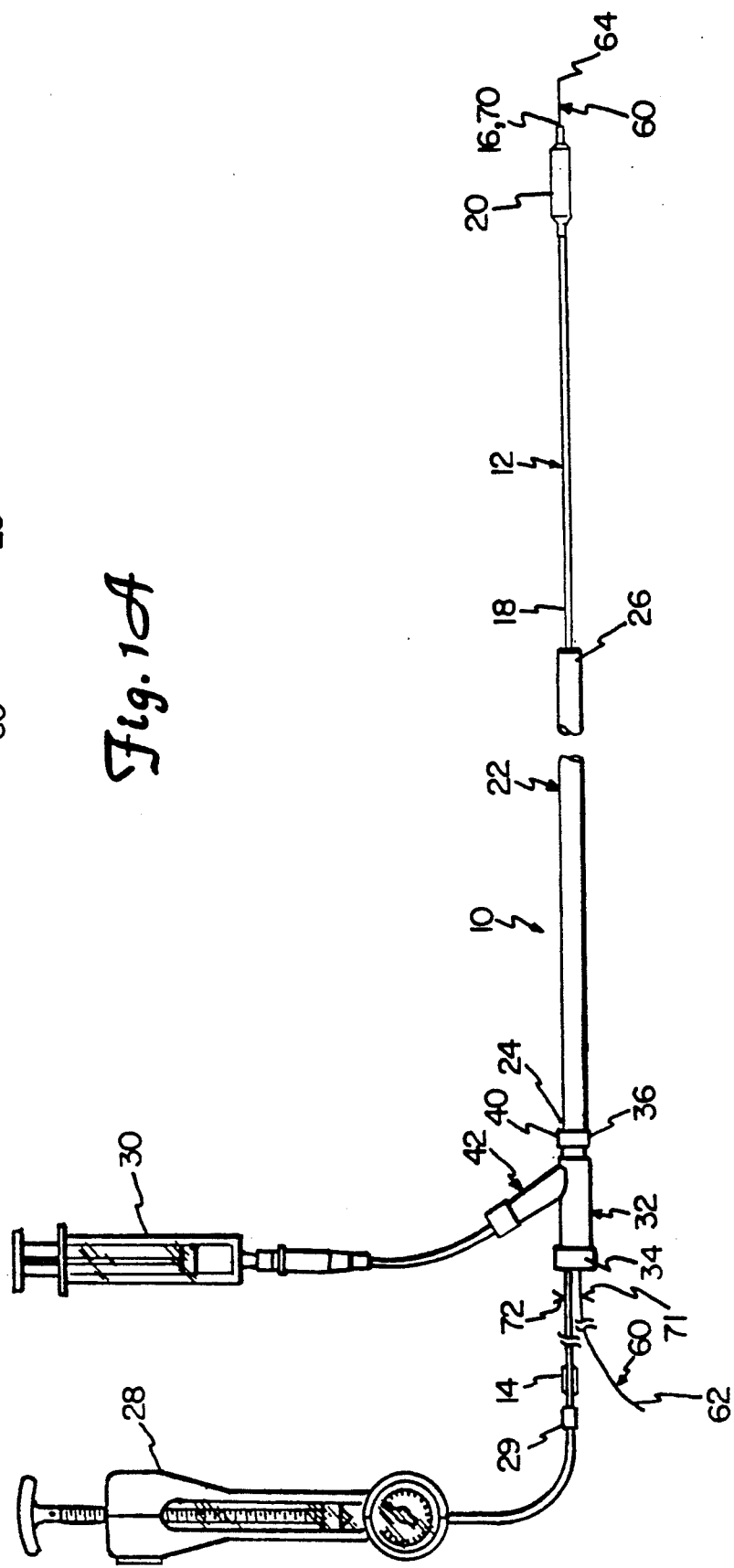

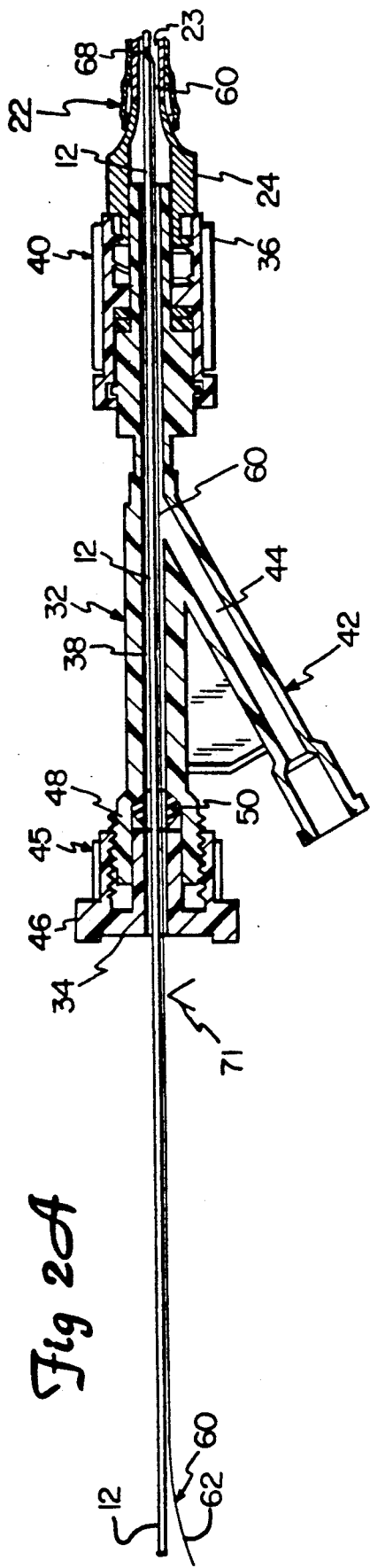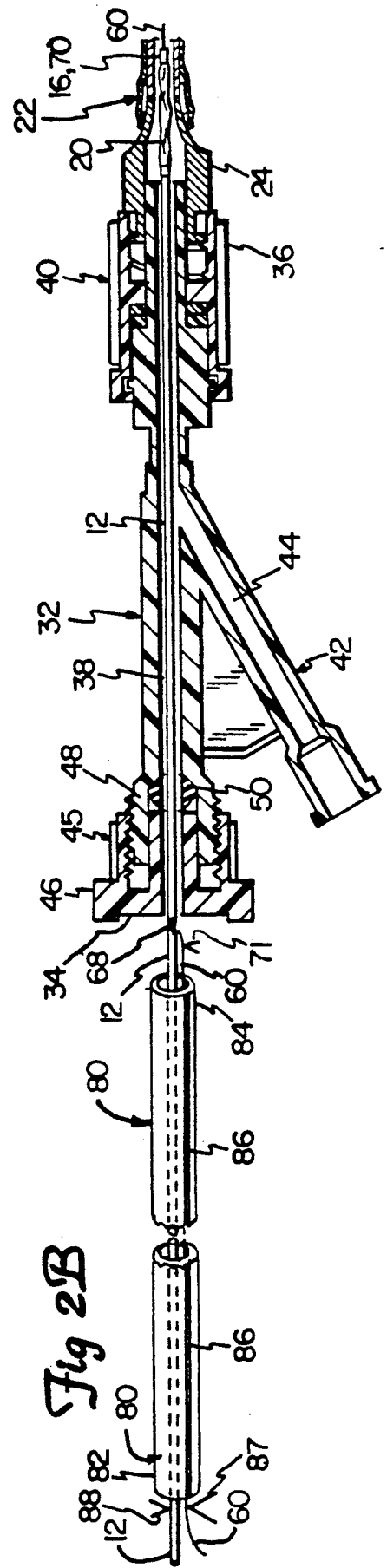

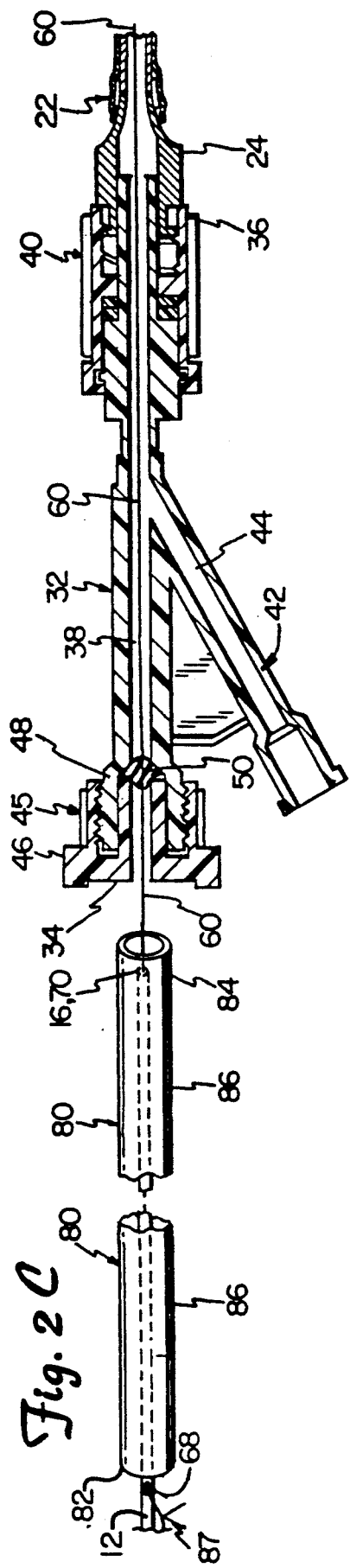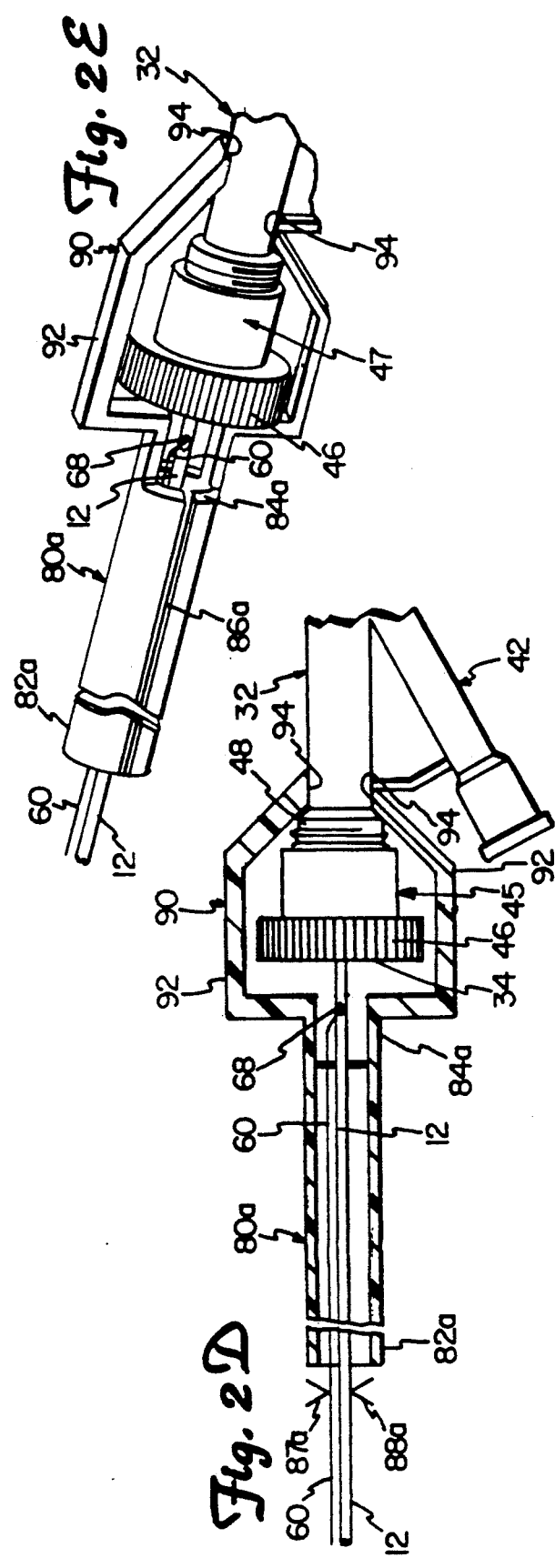

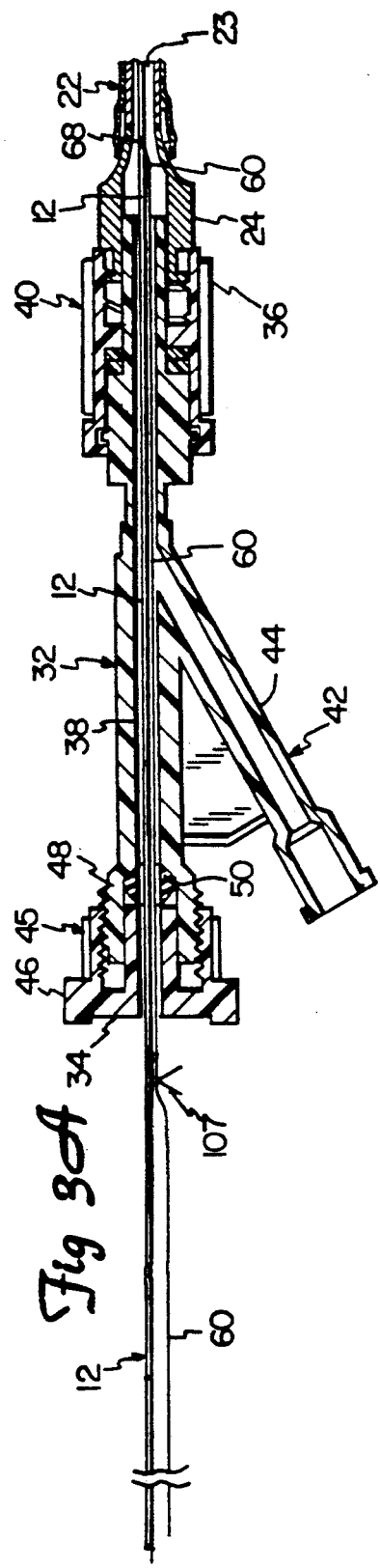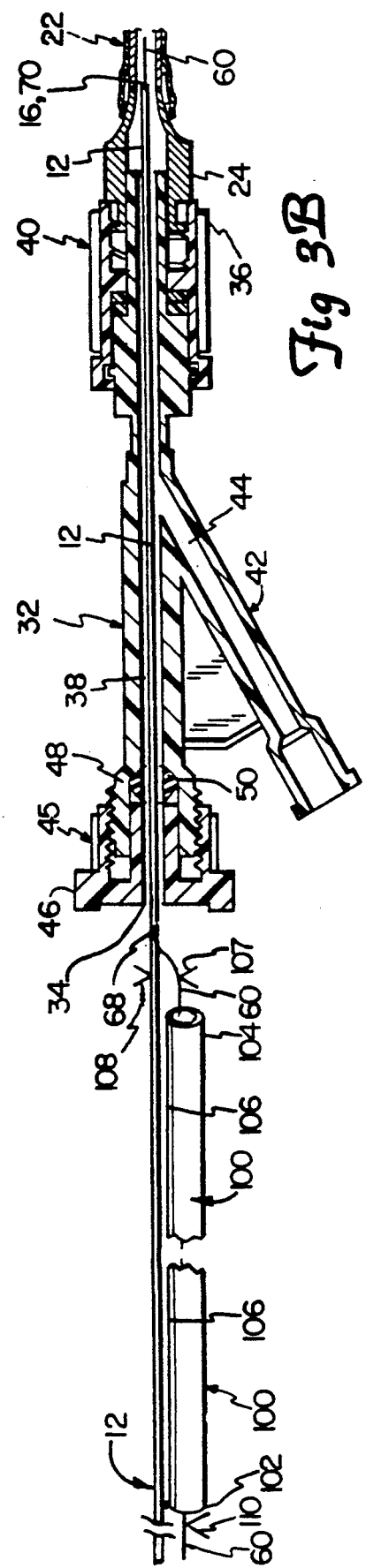

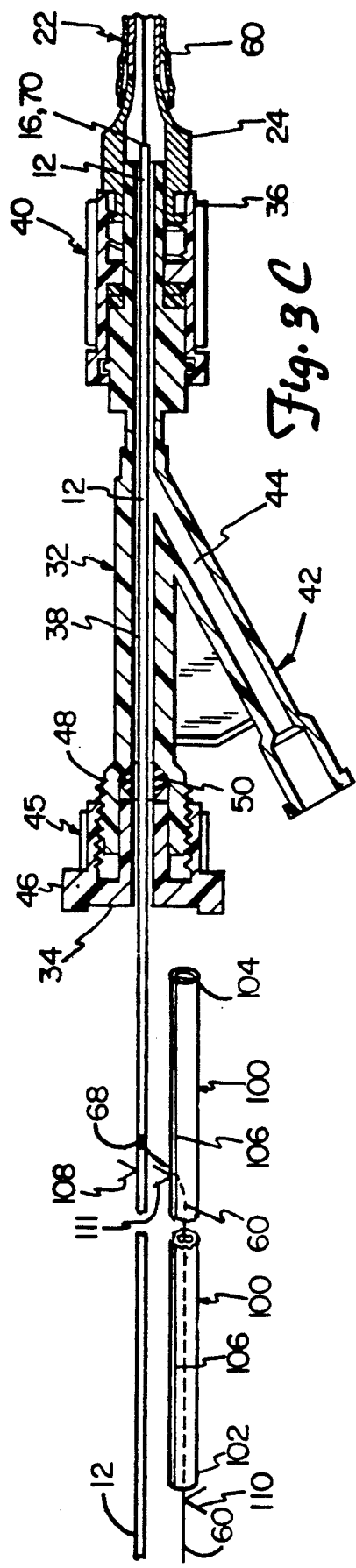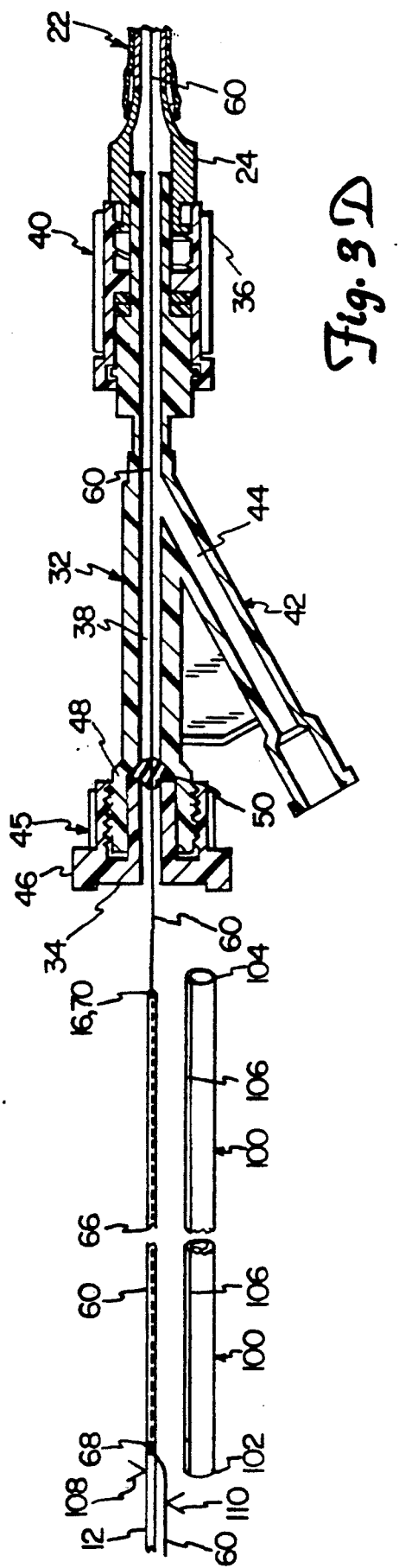

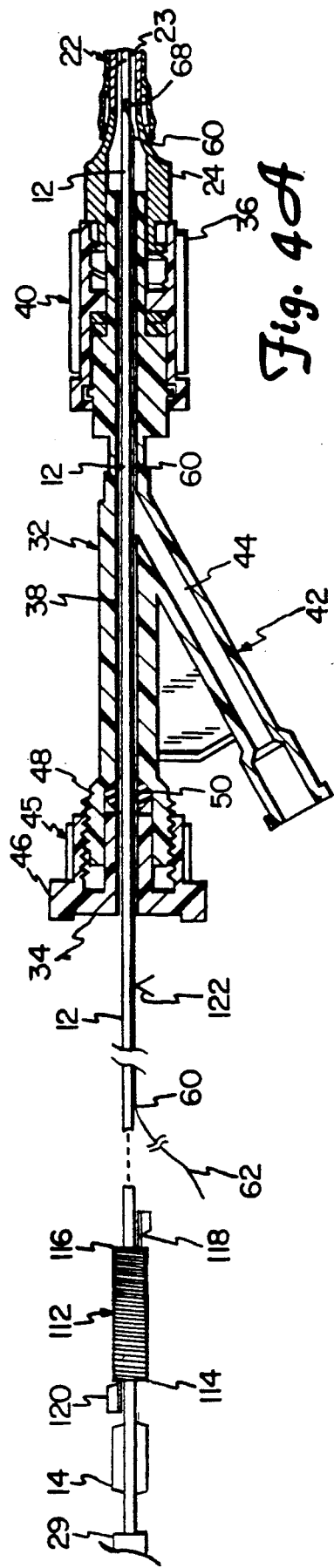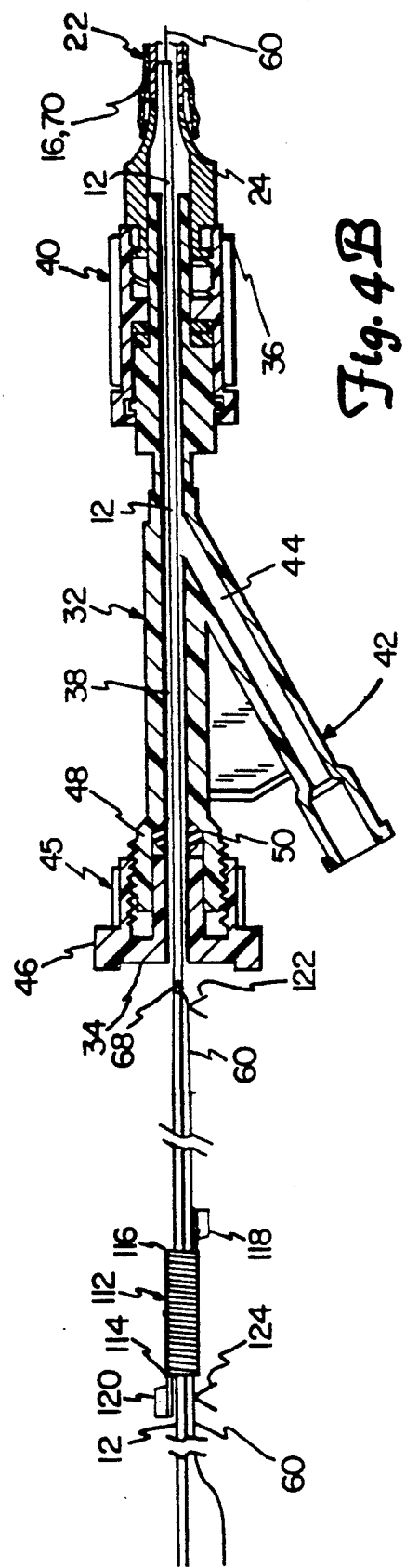

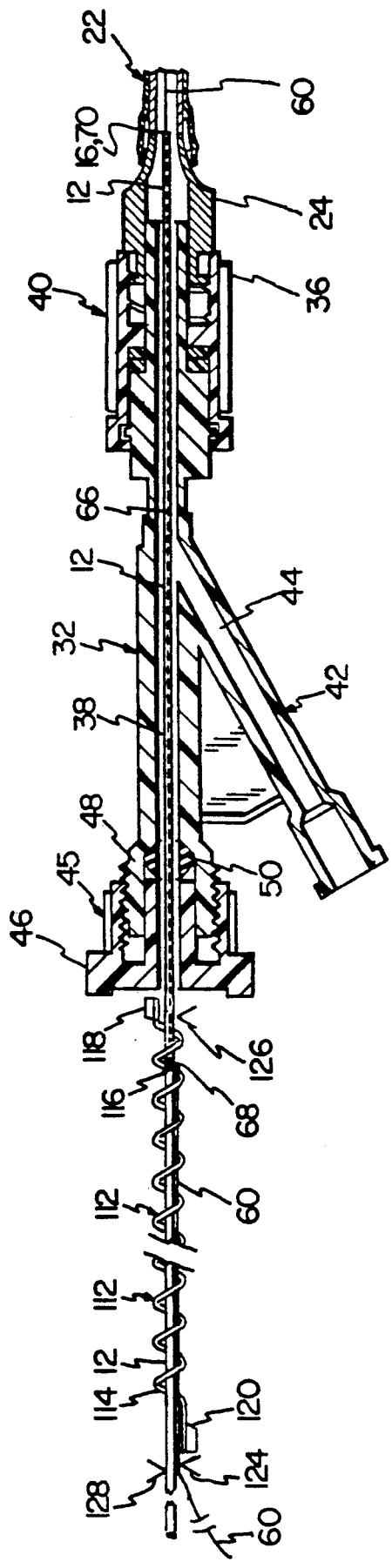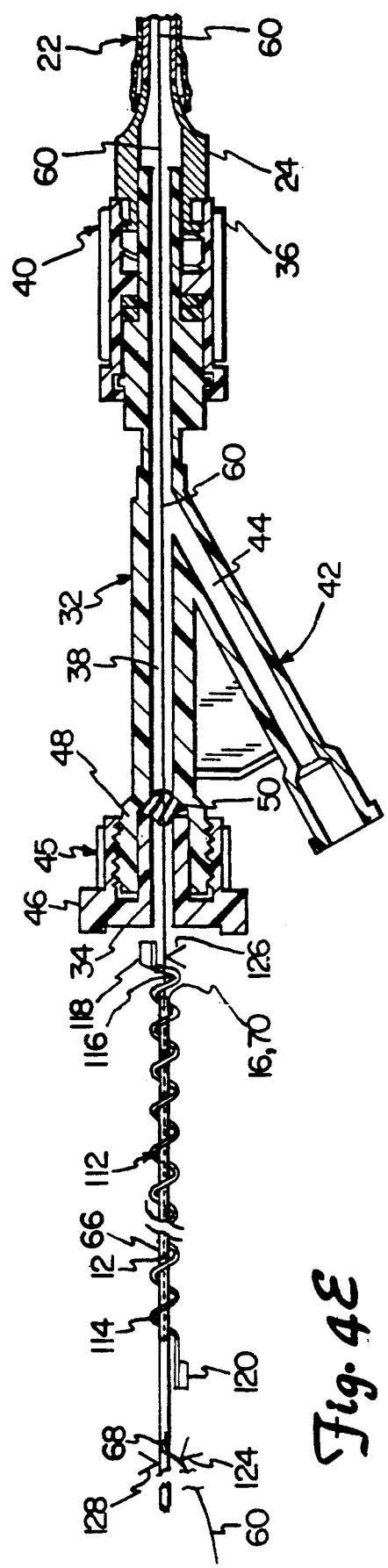

METHOD AND APPARATUS FOR PROXIMAL SUPPORT OF A GUIDE WIRE DURING CATHETER EXCHANGE

BACKGROUND OF THE INVENTION

The present invention relates to the field of angioplasty, and, in particular, to a method and apparatus for supporting a guide wire during a catheter exchange.

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. A guide catheter is positioned in the patient to establish a path to the heart. Then, the dilatation catheter is introduced into the guide catheter, and using fluoroscopy, the physician guides the dilatation catheter through the coronary arterial system until the balloon is positioned across the stenosis. The balloon is then inflated by supplying fluid pressure through an inflation lumen in the catheter to the balloon. The inflation of the balloon causes stretching of the artery and pressing of the lesion into the artery wall to re-establish acceptable blood flow through the artery, once the balloon is deflated and removed.

Two types of balloon dilatation catheters which are presently in common use are "full length over-the-wire" catheters, and "single operator exchange" style catheters. In a full length over-the-wire catheter, a guide wire lumen is provided in the catheter extending substantially the full length of the catheter. The guide wire lumen is separate from and alongside or coaxial with an inflation lumen in the catheter so that a guide wire can be used to establish the often tortuous path to and through the stenosis. The dilatation catheter is then advanced over the guide wire until the balloon is positioned across the stenosis for inflation and treatment. If a full length over-the-wire catheter in place over the guide wire is to be exchanged for a second full length over-the-wire catheter, an extension must be placed on the guide wire (or a longer guide wire must be used initially) so that a portion of the guide wire may always be held as the catheters are exchanged.

In a "single operator exchange" style angioplasty catheter, the catheter has an inflation lumen extending therethrough, but a guide wire extends through a guide wire lumen in the catheter that is only in a distal portion of the catheter. Thus, the guide wire lumen is shorter than the inflation lumen and shorter than the overall length of the catheter. The single operator exchange style catheter structure provides an alternative method for exchanging dilatation catheters, since the proximally exposed guide wire can be held while catheters are exchanged. The length of the catheter that must slide over the guide wire is lessened (the guide wire lumen is reduced to less than the length of exposed guide wire outside of the proximal end of the guide catheter.

In a single operator exchange style catheter, when one desires to exchange catheters, the guide wire is grasped proximally of a Y-adaptor of the guide catheter to maintain the guide wire in position across the stenosis. The catheter shaft is then grasped proximally of the Y-adaptor and backed off of the guide wire. After withdrawing most of the catheter out of the guide catheter, the proximal end of the guide wire lumen is positioned adjacent the proximal end of the Y-adaptor. At this point, to maintain the position of the guide wire across the stenosis while backing the balloon catheter off the guide wire, the guide wire must be grasped at some point spaced proximally of the proximal end of the guide wire lumen and the catheter withdrawn until the proximal end of the guide wire lumen is at this point of grasping. Then, the user must once again grasp the guide wire at some point spaced proximally to the proximal end of the guide wire lumen and pull the catheter proximally until the proximal end of the guide wire lumen is at this point of grasping.

This sequence must be repeated until the distal end of the guide wire lumen is proximal of the proximal end of the Y-adaptor. At this point, the guide wire is grasped or secured from longitudinal movement distally of the distal end of the guide wire lumen to maintain the position of the of the guide wire across the stenosis. With the guide wire so fixed, the dilatation balloon catheter is then withdrawn proximally from the remaining portion of the guide wire so that a second dilatation balloon catheter may be fed onto the proximal end of the guide wire and then advanced distally over the guide wire to the stenosis.

This process of repeatedly grasping the guide wire at points proximal to the proximal end of the guide wire lumen zone is tedious and time-consuming. The primary obstacle dictating the iterative grasping of the guide wire is that the guide wire will bow or buckle if the guide wire is grasped too far proximally of the proximal end of the guide wire lumen. Buckling may cause kinking of the guide wire, or may cause the distal end of the guide wire to move within the stenosis or become dislodged from the stenotic area. To avoid the buckling of the wire and to maintain the guide wire position across the stenosis, the guide wire must be grasped at relatively short distances (e.g., one inch increments) proximal to the proximal end of the guide wire lumen, resulting in the numerous repetitive iterations of proximal grasping of the guide wire. Thus, although the single operator exchange style catheters provide an alternative catheter exchange arrangement, they do not necessarily overcome the difficulty of maintaining guide wire position across the stenosis while removing the catheter from the guide wire, as well as avoiding or minimizing the danger of kinking, bowing or buckling the guide wire.

SUMMARY OF THE INVENTION

The present invention includes a method and apparatus for providing proximal support for a guide wire during a catheter exchange. The present invention simplifies removal of a single operator exchange style catheter from a guide wire while maintaining the guide wire in fixed position across an arterial stenosis.

The present invention includes a method for withdrawing a catheter from a guide catheter, having a guide catheter lumen, while restraining a catheter guide wire from longitudinal and lateral bowing movement relative to the guide catheter lumen. This inventive method is used in a catheter system in which the catheter has a guide wire lumen shorter than a length of the catheter. The guide wire extends through the guide wire lumen and extends with the catheter through the lumen of the guide catheter.

In the inventive method, constraining means for constraining the guide wire is provided and positioned proximal to the guide catheter substantially extending around the guide wire to prevent the guide wire from bowing. The guide wire is then held proximally adjacent the constraining means to prevent the guide wire from moving longitudinally relative to the guide catheter. While holding the guide wire, the catheter is withdrawn from the guide catheter in a proximal, axial direction until a distal end of the guide wire lumen is proximal of the guide catheter. Next, the guide wire is held at a point distal of the guide wire lumen to prevent the guide wire from moving longitudinally relative to the guide catheter lumen. The guide wire is then released proximally adjacent the constraining means. Finally, the catheter is withdrawn in the proximal axial direction until the guide wire lumen is free from the guide wire.

In addition, the guide catheter may be provided with a proximal fitting (e.g., a Y-adaptor) connected to a proximal end of the guide catheter. The proximal fitting has a lumen extending therethrough that is in fluid communication with the lumen of the guide catheter, the guide wire and catheter extending through both the guide catheter lumen and proximal fitting lumen. The constraining means is used in a manner similar to the inventive method just described except that the constraining means is positioned proximally adjacent the proximal fitting instead of just proximal to the proximal end of the guide catheter.

In one preferred embodiment, the constraining means comprises an elongate sleeve. The sleeve has an inner diameter large enough to encompass both the guide wire and the catheter. In this embodiment, the sleeve includes an elongate slit in the sleeve extending from a proximal end to a distal end thereof.

The apparatus of the present invention is for use with an intralumenal catheter system which has an intralumenal guide wire and a catheter. The catheter has a guide wire lumen therein for slidably receiving the guide wire, with both the guide wire and the catheter guide wire lumen extending longitudinally through a lumen of a guide catheter. The apparatus is adapted to allow a physician to maintain the guide wire in the desired position relative to the guide catheter during withdrawal of the catheter from the guide catheter. The apparatus comprises constraining means positioned generally adjacent a proximal end of the guide catheter and substantially surrounding a segment of the guide wire. As in the inventive method, a proximal fitting member may be connected to the proximal end of the guide catheter and the constraining means positioned proximally adjacent the proximal fitting.

In one preferred embodiment of the present invention, the constraining means comprises an elongate sleeve. The sleeve has an inner lumen which is suitable for providing lateral support to the guide wire during proximal withdrawal of the catheter from the guide catheter. The inner lumen of the sleeve is sized to encompass both the guide wire and dilatation catheter. Likewise another embodiment comprises an elongate sleeve having an inner lumen sized to encompass the guide wire only.

In another embodiment, the constraining means comprises an elongate coil that encompasses the dilatation balloon catheter and the guide wire to provide proximal support to the guide wire during exchange of the balloon catheters.

BRIEF DESCRIPTION OF THE DRAWINGS

The invention will be further described with reference to the accompanying drawings where like numbers refer to like parts in several views and wherein:

FIG. 1A is a view in side elevation of a dilatation balloon catheter system used with the present invention.

FIG. 1B is an enlarged fragmentary detail of a portion of FIG. 1A illustrating a single operator exchange style dilatation catheter and guide wire disposed in a guide catheter.

FIG. 2A is a sectional view of the proximal end of the guide catheter and a Y-adaptor mounted thereto, with the dilatation catheter and guide wire extending therethrough.

FIG. 2B is a sectional view like FIG. 2A, incorporating an elongate sleeve of the present invention over the dilatation catheter and guide wire proximally of the Y-adaptor.

FIG. 2C is a sectional view like FIG. 2A, illustrating the proximal end of the guide wire lumen proximal to the elongate sleeve of the present invention.

FIG. 2D is a view in section similar to 2A, and illustrating an elongate sleeve of the present invention with a clamp mounted on a distal end of the sleeve secured to the proximal end of the Y-adaptor.

FIG. 2E is a perspective view of the elongate sleeve with a clamp at the proximal end thereof secured to the proximal end of the Y-adaptor.

FIG. 3A is a sectional view like FIG. 2A.

FIG. 3B is a sectional view like FIG. 3A, and illustrating an elongate sleeve of the present invention encompassing only the guide wire proximal to the proximal end of the guide wire lumen of the dilatation catheter.

FIG. 3C is a sectional view like FIG. 3A, illustrating the elongate sleeve of the present invention being peeled away from the guide wire as the dilatation catheter is withdrawn proximally relative to the guide wire so that the proximal end of the guide wire lumen of the catheter passes alongside the sleeve.

FIG. 3D is a sectional view like FIG. 3A, illustrating the elongate sleeve of the present invention completely separated from the dilatation catheter, which has been fully withdrawn from the Y-adaptor.

FIG. 4A is a view in section similar to FIG. 2A, illustrating a compressed coil of the present invention adjacent a proximal end of the catheter.

FIG. 4B is a view in section like FIG. 4A, illustrating the coil at some point spaced proximally from a proximal end of the Y-adaptor and encompassing both the catheter and the guide wire.

FIG. 4C is a view in section like FIG. 4A, illustrating the coil of the present invention in an expanded state encompassing the catheter and guide wire.

FIG. 4E is a view in section like FIG. 4A, illustrating the proximal end of the guide wire lumen being adjacent a distal end of the coil of the present invention in its expanded state.

Figure 4D:
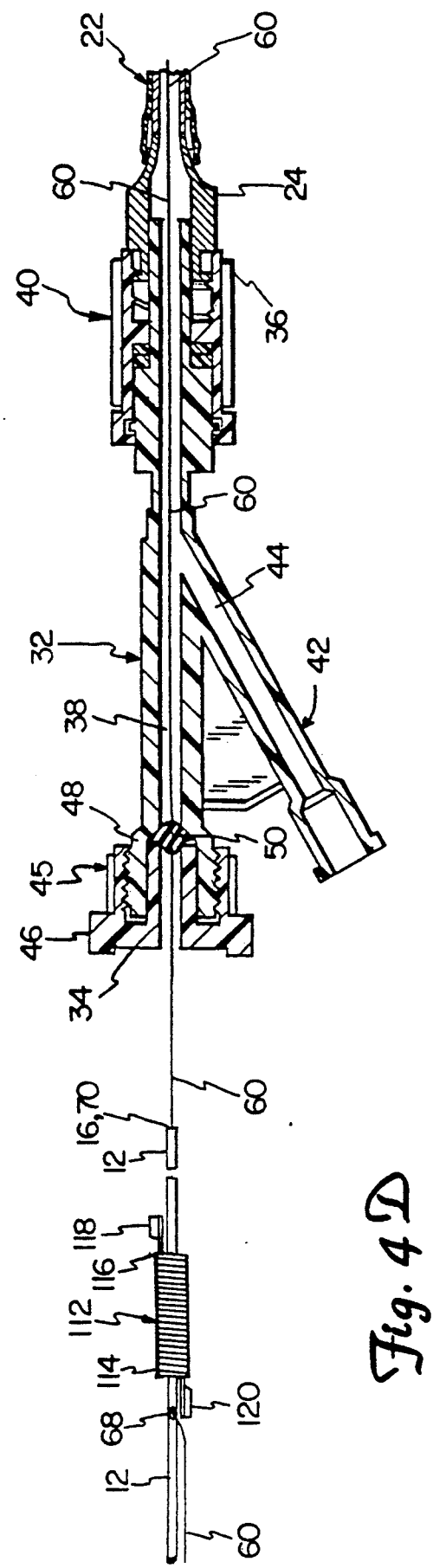
FIG. 4D is a view in section like FIG. 4A, illustrating the coil of the present invention in a non-expanded state adjacent the proximal end of the guide wire lumen.

While the above identified drawing figures set forth several preferred embodiments, other embodiments of the present invention are also contemplated, as noted in the discussion. In all cases, this disclosure presents illustrated embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity.

DETAILED DESCRIPTION OF THE PREFERRED EMBODIMENTS

The present invention includes a method and apparatus for providing proximal support for a guide wire during a catheter exchange. The present invention simplifies removal of a single operator exchange style catheter from a guide wire while maintaining the guide wire in fixed position across an arterial stenosis. To fully understand the advantages of the present invention, it is necessary to review the process for conducting a typical catheter exchange for a single operator style dilatation balloon catheter. This will highlight the complications and problems that arise during these catheter exchanges and simultaneously provide insight into the advantages and benefits of performing a catheter exchange with the present invention.

I. A TYPICAL CATHETER EXCHANGE FOR A SINGLE OPERATOR TYPE DILATATION BALLOON CATHETER

A proximal support for a catheter exchange guide wire of the present invention is used with an angioplasty single operator exchange style catheter system of the type illustrated generally in FIG. 1A at 10. The catheter system is used in angioplasty procedures to treat stenoses in the coronary arteries or other vascular branch systems. The catheter system as seen in FIG. 1A includes a dilatation catheter 12 having a proximal end 14 and a distal end 16. A shaft 18 extends between the proximal end 14 and distal end 16 and defines an inflation lumen 19 which is in fluid communication with the interior of a dilatation balloon 20 disposed at the distal end 16 of catheter 12. The catheter system also includes a catheter introduction/guide sheath or guide catheter 22, which has a proximal end 24 and a distal end 26 with a lumen 23 extending therebetween.

In an angioplasty procedure, the guide catheter 22 is used to establish a path to the heart. The distal end 26 of guide catheter 22 is typically inserted into the femoral artery in the thigh area and maneuvered through the vascular system until the distal end 26 is near the heart. The proximal end 24 of the guide catheter 22 remains outside of the patient providing an access point to the guide catheter lumen 23.

The dilatation catheter 12 is introduced into the patient through the guide catheter 22. The distal end 16 of catheter 12 is inserted through the proximal end 24 of the guide catheter 22 and pushed through the guide catheter 22 until the distal end 16 of catheter 12 is adjacent the distal end 26 of guide catheter 22. A radiopaque dye is then used in combination with x-ray fluoroscopy to help visualize the coronary artery system for further maneuvering of catheter 12. The dye is supplied to the arterial pathway through the guide catheter 22 by a syringe 30 connected to the proximal end 24 of the guide catheter 22 for fluid communication therebetween. Using fluoroscopy, a physician guides the dilatation catheter 12 through the coronary arterial system until the balloon 20 is positioned across the stenosis.

To treat the stenosis, the balloon 20 is inflated by supplying fluid pressure through inflation lumen 19 with an inflation device 28 connected to the proximal end 14 of catheter 12 by an adaptor 29. Inflating the balloon 20 dilates the stenosis by stretching the artery and simultaneously pressing the lesion into the artery wall. Once the stenosis has been treated, a physician deflates the balloon 20 by reducing the fluid pressure with inflation device 28. The catheter 12 is then maneuvered out of the coronary artery system and removed from the guide catheter 22.

As seen in FIG. 1A, a Y-adaptor (or proximal fitting) 32 provides an access point for catheter 12 to be inserted into guide catheter 22. As seen in FIGS. 2A–2E, the Y-adaptor 32 has a proximal end 34 and a distal end 36 with a proximal lumen 38 extending therebetween and in fluid communication with guide catheter lumen 23. The distal end 36 of Y-adaptor 32 is rotatably mounted to the proximal end 24 of guide catheter 22 by a rotatable adaptor 40 such that a seal is maintained between the proximal lumen 38 and the guide catheter lumen 23. The catheter 12 extends through the Y-adaptor proximal lumen 38 into the guide catheter lumen 23. An extension arm 42 of Y-adaptor 32 defines a second lumen 44 to provide a path for fluid communication between the syringe 30 and the proximal lumen 38 and guide catheter lumen 23.

At the proximal end 34 of Y-adaptor 32, a hemostatic sealing valve 45 includes a knob 46 which is threadedly mounted to a threaded valve member 48 which carries a compressible O-ring 50. As seen in FIG. 2C, the O-ring 50 is adapted to be compressed by member 48 to sealingly engage catheter 12 and other intravascular devices (such as a guide wire) extending through proximal lumen 38 and guide catheter lumen 23. This engagement limits longitudinal movement of such devices relative to the Y-adaptor 32. When valve 45 is closed (FIG. 2C), i.e., the O-ring 50 is compressed and the proximal end 34 of Y-adaptor lumen 38 is sealed shut. The compressed O-ring 50 of valve 45 maintains the radiopaque dye or other fluids within the guide catheter lumen 23. When the valve 45 is open (FIG. 2B), i.e., the O-ring 50 is relaxed and the proximal end 34 of Y-adaptor lumen 38 is open permitting the longitudinal movement of intravascular devices through proximal lumen 38.

Although not previously identified, in single operator exchange catheter systems, a steerable guide wire 60 is used in combination with a guide wire lumen 66 of catheter 12 (see FIG. 1B) to establish a path for catheter 12 beyond the distal end 26 of guide catheter 22 through the coronary artery system up to and through the stenosis. The guide wire 60 has a proximal end 62 and a distal end 64 (see FIG. 1A). The guide wire lumen 66 is formed in a distal portion of catheter 12 (FIG. 1B), and has a proximal end 68 (FIG. 1B) and a distal end 70 (FIG. 1A).

In a single operator catheter, the guide wire lumen 66 has a length shorter than the length of catheter 12 and, as shown (FIG. 1B or FIG. 2B), the proximal end 68 of guide wire lumen 66 is located nearer the distal end 16 of catheter 12 than the proximal end 14 thereof. For example, the proximal end 68 of guide wire lumen 66 may be located approximately 35 centimeters proximal to the distal end 16 of catheter 12 (having a full length of about 135 centimeters) or at any point closer to or further from the distal end 16 of the catheter 12.

In a typical angioplasty procedure using a single operator exchange style catheter system having a guide wire 60 and guide wire lumen 66, the guide catheter 22 is positioned within the vascular system to establish a path to the heart as previously described. Next, the distal end 64 of guide wire 60 is inserted into the proximal end 34 of Y-adaptor 32. The physician grasps the guide wire 60 proximally of the proximal end 34 of Y-adaptor 32 and pushes the guide wire 60 distally through the Y-adaptor 32 and guide catheter 22 until the distal end 64 of guide wire 60 is positioned adjacent and within the distal end 26 of guide catheter 22. Next, using the previously described technique of fluoroscopy, the physician further maneuvers the distal end 64 of guide wire 60 distally through the tortuous coronary artery system to and across the stenosis. The sealing valve 45 is then closed to seal the proximal end 34 of the Y-adaptor lumen 38. The proximal end 62 of guide wire 60 extends out of the proximal end 34 of Y-adaptor 32 (like shown in FIG. IA) for a length longer than the length of guide wire lumen 66 (e.g. longer than 35 cm, such as 40 cm).

Once the guide wire 60 has established a path from the femoral artery through the guide catheter 22 and the coronary artery system to the stenosis, the catheter 12 is ready to be introduced into the patient's vascular system. First the valve 45 remains closed to seal shut the guide catheter lumen 23 (and Y-adaptor lumen 38) to prevent "back-bleeding" of body fluids and other fluids such as radiopaque dye and saline solution. The closed valve 45 also restrains the guide wire 60 from longitudinally movement relative to the Y-adaptor 32 thereby maintaining the guide wire 60 in position across the stenosis. The physician may also continue grasping the guide wire 60 at a grasping point 71 (FIG. 2A) proximally adjacent to the proximal end 34 of Y-adaptor 32 to further restrain the guide wire 60 from such longitudinal movement relative to Y-adaptor 32.

While still restraining the guide wire 60, the distal end 70 of guide wire lumen 66 is loaded over the proximal end 62 of guide wire 60. The catheter 12 is then pushed distally over guide wire 60 longitudinally relative to the guide wire 60 such that the guide wire lumen 66 slides over the guide wire 60 and the proximal end 62 of guide wire 60 exits the proximal end 68 of guide wire lumen 66. The grasping of guide wire 60 at 71 is released and then the exposed proximal end 62 of the guide wire 60 is grasped again proximal to the proximal end 68 of guide wire lumen 66. In addition, the valve 45 is opened to further release the guide wire 60 from being restrained and to open the proximal end 34 of Y-adaptor lumen 38.

While still grasping the guide wire 60, the guide wire lumen 66 of catheter 12 is then moved distally over guide wire 60 leading catheter 12 through Y-adaptor lumen 38 (so that both the guide wire 60 and guide wire lumen 66 extend side by side through the lumen 38), guide catheter 22, and the coronary arteries (by fluoroscopy) until the balloon 20 of catheter 12 is positioned across the stenosis. At this point, the sealing valve 45 is once again closed to seal off the Y-adaptor lumen 38 and guide catheter lumen 23. As previously described, the balloon 20 is then inflated to dilate the stenosis and thereby re-establish acceptable blood flow through the artery (occurring once the balloon 20 is deflated and catheter 12 is later removed).

As an alternative to the previously described advancement of the guide wire 60 and catheter 12, the guide wire 60 and catheter 12 may be simultaneously advanced through the guide catheter 22. In this "pre-loaded catheter" advancement technique, the catheter 12 is first loaded onto guide wire 60 before either the wire 60 or catheter 12 are inserted into the Y-adaptor 32 and advanced through guide catheter 22. First, the proximal end 62 of guide wire 60 is inserted into the distal end 70 of guide wire lumen 66. The guide wire 60 is then fed through the guide wire lumen 66 proximally longitudinally relative to the catheter 12 by inching the guide wire 60 in small increments through lumen 66 (to avoid kinking) until the proximal end 62 of guide wire 60 exits the proximal end 68 of guide wire lumen 66. Next, the physician pulls the guide wire 60 proximally through the guide wire lumen 66 until the distal end 64 of guide wire 60 is just within the distal end 70 of guide wire lumen 66.

In this "pre-loaded catheter" technique, the Y-adaptor 32 has not yet been connected to the guide catheter 22 but remains free standing. Thus, the distal end 16 of catheter 12 (along with the distal end 64 of guide wire 60 within lumen 66 and the balloon 20 fully deflated) are inserted into the proximal end 34 of Y-adaptor 32 (with valve 45 open) and carefully advanced through the Y-adaptor 32 until the distal end 36 of Y-adaptor 32 is proximal to the proximal end 68 of guide wire lumen 66. Next, the distal end 16 of catheter 12 (with guide wire 60) is inserted into the proximal end 24 of guide catheter 22 and advanced through guide catheter lumen 23 until the Y-adaptor 32 is proximally adjacent the proximal end 24 of guide catheter 22. The rotatable adaptor 40 of Y-adaptor 32 is then connected to the proximal end 24 of guide catheter 22.

The physician then advances the guide wire 60 through guide wire lumen 66 until the distal end 64 of guide wire 60 is just distal to the distal end 70 of the guide wire lumen 66.

The physician then grasps both the guide wire 60 and catheter 12 proximally of the proximal end 34 of Y-adaptor 32 and pushes (by "inching") the guide wire 60 and catheter 12 distally through the guide catheter lumen 23 until the distal end 64 of guide wire 60 is just within the distal end 26 of guide catheter 22. Next, the guide wire 60 is maneuvered through the coronary arteries (by using fluoroscopy) until the guide wire 60 crosses the stenosis. The balloon 20 of catheter 12 is then advanced to a desired position across the stenosis. Next, the sealing valve 45 is once again closed to seal the Y-adaptor lumen 38. As previously described, the balloon 20 is then inflated to dilate the stenosis and thereby re-establish acceptable blood flow through the artery (occurring once the balloon 20 is deflated and catheter 12 is later removed).

Sometimes the lesion does not dilate to an anticipated or desired size. In this instance, the catheter 12 may be exchanged for another catheter with a balloon having a different size. During such catheter exchange procedures, it is desirable to maintain the position of the guide wire 60 across the stenosis. The wire will act to foreclose the possibility of a possible abrupt closure of a partially dilated lesion when the balloon catheter has been withdrawn after an initial dilatation.

To exchange catheters, the physician opens sealing valve 45 to open the proximal end 34 of Y-adaptor lumen 38. Next, while the guide wire 60 is still grasped proximally of the proximal end 34 of Y-adaptor 32 (at 71 in FIGS. IA and 2A), the catheter 12 is separately grasped proximally of the proximal end 34 of Y-adaptor 32 (at 72 in FIG. 1A) and pulled proximally in an axial direction off the guide wire 60 out of the coronary artery system and the guide catheter 22. The catheter 12 is withdrawn proximally until the proximal end 68 of guide wire lumen 66 is positioned adjacent the proximal end 34 of Y-adaptor 32 and just distal to the grasping point 71 on guide wire 60 (FIG. 2B).

At this point, to maintain the position of the guide wire 60 across the stenosis while backing the catheter 12 off the guide wire 60, the guide wire 60 must be grasped at some point slightly spaced proximally of the proximal end 68 of the guide wire lumen 66 (e.g., about an inch) and the catheter 12 withdrawn until the proximal end 68 of the guide wire lumen 66 is at this point of grasping. The last step is repeated until the distal end 16 of the catheter 12 is proximal of the proximal end 34 of the Y-adaptor 32. The sealing valve 45 is then closed to prevent the guide wire 60 from longitudinal movement distally of the distal end 16 of the catheter 12 thereby maintaining the position of the guide wire 60 across the stenosis. With the guide wire 60 so fixed, the catheter 12 is then withdrawn proximally from the remaining portion of the guide wire 60 so that a second dilatation catheter 12 may be fed onto the proximal end 62 of the guide wire 60 and then advanced distally over the guide wire 60 to the stenosis (for treatment thereof).

The efficiency of this process of repeatedly grasping the guide wire 60 (during removal of catheter 12 from guide wire 60) at points proximal to the proximal end 68 of the guide wire lumen 66 is dictated by the tendency of the guide wire 60 to bow or buckle if the guide wire 60 is grasped too far proximally of the proximal end 68 of the guide wire lumen 66 during withdrawal of catheter 12. Buckling (or bowing) may cause kinking of the guide wire 60, or may cause the distal end 62 of the guide wire 60 to move within the stenosis, or to become dislodged from the stenotic area. To avoid the buckling and bowing of the guide wire 60 and to maintain the guide wire 60 in position across the stenosis, the guide wire 60 must be grasped at relatively short distances (e.g., one inch increments) proximal to the proximal end 68 of the guide wire lumen 66, resulting in the numerous repetitive iterations of proximal grasping of the guide wire 60. This continual regrasping takes considerable time and effort during an angioplasty procedure. Moreover, the sealing valve 45 must remain open while "inching" off the catheter 12 resulting in back bleeding of the radiopaque dye and other fluids through the guide catheter lumen 23 and Y-adaptor lumen 38.

II. PROXIMAL SUPPORT OF A GUIDE WIRE DURING A CATHETER EXCHANGE

The present invention provides constraining means for providing proximal support for a guide wire during catheter exchanges to simplify removal of a single operator exchange style catheter from a guide wire. The constraining means helps maintain the guide wire in a fixed position across an arterial stenosis. During the withdrawal of a single operator exchange style catheter off a guide wire in a catheter exchange, the constraining means is positioned alongside or substantially encompasses the catheter proximally of a guide catheter lumen to support the guide wire. The constraining means prevents he guide wire from buckling or bowing laterally away from the catheter and alleviates the necessity of repeatedly grasping the guide wire to "inch" the guide wire lumen of the single operator exchange style catheter out of the guide catheter lumen while securing the guide wire from longitudinal movement across the stenosis. The use of the present invention eliminates many steps in a catheter exchange, saving time and effort.

Moreover, use of the present invention reduces the likelihood of the guide wire being dislodged from the stenosis, or the guide wire kinking caused by buckling of the guide wire when the guide wire lumen of the single operator exchange style catheter is backed off the guide wire proximally of the guide catheter lumen.

A. A First Exchange Sleeve Of The Present Invention

As seen in FIGS. 2B–2E, a first exchange sleeve 80 of the present invention encompasses both the catheter 12 and guide wire 60 and is positioned proximal to the proximal end 34 of Y-adaptor 32. The first exchange sleeve 80 has a proximal end 82 and a distal end 84 with a lumen extending therebetween. The first exchange sleeve 80 is an elongated tube made of a polymer material such as polyethylene, and has an inner lumen with a diameter sufficient to encompass both the guide wire 60 and the catheter 12. The first exchange sleeve 80 has an elongate longitudinal slit 86 formed in a wall of the sleeve 80 extending from the proximal end 82 to the distal end 84 of the first exchange sleeve 80.

The first exchange sleeve 80 preferably has a length approximately the same as a length of the guide wire lumen 66 (e.g., 35 cm for a guide wire lumen 66 length of 35 cm respectively). Alternatively, the exchange sleeve 80 also can have a length appreciably longer than the length of the guide wire lumen 66. Further, an exchange sleeve 80 shorter than the length of the guide wire lumen 66 would work although this will tend to diminish the efficiencies achieved by the inventive exchange sleeve.

To exchange catheters during an angioplasty procedure, the physician first deflates balloon 20 to its lowest possible profile and then grasps the guide wire 60 proximal to the proximal end 34 of the Y-adaptor 32 (as at 71 in FIGS. IA and 2A) to maintain the guide wire 60 in position across the stenosis during the removal of the catheter 12. The sealing valve 45 is then opened to open the proximal end 34 of Y-adaptor lumen 38. Next, while still holding the guide wire 60 in position, the catheter 12 is withdrawn proximally over the guide wire 60 away from the stenosis and through the guide catheter 22 and Y-adaptor lumen 38 until the proximal end 68 of guide wire lumen 66 is adjacent the proximal end 34 of the Y-adaptor 32. Typically, as seen in FIG. 2B, the catheter 12 is moved proximally until the proximal end 68 of guide wire lumen 66 is partially visible from the proximal end 34 of the Y-adaptor 32 indicating to the physician that the guide wire lumen 66 is adjacent the proximal end 34 of adaptor 32.

At this point, while still holding guide wire 60 in a fixed position at grasp point 71, the first exchange sleeve 80 is mounted over the catheter 12 and the guide wire 60 by laterally inserting the guide wire 60 and catheter 12 through the longitudinal slit 86 of sleeve 80 (the sleeve 80 is sufficiently flexible to permit separation of the slit 86 and such insertion. However, the first exchange sleeve 80 may be loaded onto the catheter 12 and guide wire 60 before the catheter 12 is substantially removed from the guide catheter 22.

After the first exchange sleeve 80 has been loaded over the guide wire 60 and catheter 12, the distal end 84 of sleeve 80 is moved distally over both the guide wire 60 and catheter 12 until proximally adjacent the fingers which are still holding guide wire 60 at 71. The guide wire 60 is then released at 71 and grasped proximal to the proximal end 82 of sleeve 80 (as at 87 in FIG. 2B). The catheter 12 is separately grasped proximal to the proximal end 82 of sleeve 80 (as at 88 in FIG. 2B). The guide wire 60 is then held in a fixed position longitudinally relative to the Y-adaptor 32, while the catheter 12 is pulled proximally over the guide wire 60 until a distal end 70 of the guide wire lumen 66 (in this catheter 12 as illustrated, same as distal end 16 of catheter 12) is positioned proximal to the proximal end 34 of Y-adaptor 32. At this point the proximal end 68 of guide wire lumen 66 is located adjacent to the grasping point 87 on guide wire 60, as seen in FIG. 2C.

During this step, the first exchange sleeve 80 is restrained from substantial longitudinal movement relative to the guide wire 60 because the proximal end 82 of sleeve 80 abuts the fingers of the physician at grasping point 87. The first exchange sleeve 80 may also be restrained from longitudinal movement by partially pinching the sleeve 80 at its proximal end 82 along with the grasping of guide wire 60 at grasping point 87 such that the sleeve 80 is restrained from moving proximally, yet the catheter 12 may still be withdrawn proximally through the sleeve 80.

While the catheter 12 is being moved proximally during this phase of the exchange, the sleeve 80 provides support to guide wire 60 preventing the guide wire moving laterally away from catheter 12. The sleeve 80 prevents the guide wire 60 from bowing or buckling as the catheter 12 is moved proximally in an axial direction longitudinally relative to the guide wire 60. The sleeve 80 helps maintain the position of the guide wire 60 across the stenosis so that the tortuous vascular path need not be re-established. In addition, the sleeve 80 also prevents kinking of guide wire 60 (that may occur as a result of buckling), thereby maintaining the maneuverability of the guide wire 60 that might otherwise be lost if a kink was formed in the guide wire 60. The sleeve 80 also prevents the distal end 64 of the guide wire 60 from irregularly moving within the stenotic area of the artery which might cause damage to the vessel walls.

Once the distal end 70 of the guide wire lumen 66 is proximal to the proximal end 34 of the Y-adaptor 32, valve 45 is closed to seal shut the Y-adaptor lumen 38 and to fix the guide wire 60 in position within the Y-adaptor lumen 38 (as seen in FIG. 2C) longitudinally relative to the Y-adaptor 32, thereby maintaining the position of the guide wire 60 across the stenosis. The guide wire 60 can then be released proximally of the proximal end 82 of the first exchange sleeve 80 (at 87). The catheter 12 is further moved proximally over guide wire 60 until the guide wire lumen 66 is removed completely from the guide wire 60. The first exchange sleeve 80 may preferably be removed from the guide wire 60 with the catheter 12, or the sleeve 80 may be grasped and held on the guide wire 60 when the catheter 12 is removed completely from the guide wire 60.

Thereafter, a guide wire lumen 66 of a second catheter 12 may be loaded over the proximal end 62 of the guide wire 60 and moved distally over the guide wire 60 until the distal end 16 of the catheter 12 (or if the same, the distal end 70 of guide wire lumen 66) is proximally adjacent the proximal end 34 of the Y-adaptor 32 or abuts the compressed O-ring 50. If the sleeve 80 was held on the guide wire 60 when the first catheter 12 was removed, then during the loading of the second catheter 12, the sleeve 80 is still held on the guide wire 60 while the distal end 16 of catheter 12 is inserted into the proximal end 82 of sleeve 80 then pushed through sleeve 80 over guide wire 60. Next, the guide wire 60 is grasped proximally of the proximal end 68 of guide wire lumen 66 to hold the guide wire 60 in a fixed position longitudinally relative to the Y-adaptor 32. The valve 45 is then opened to release guide wire 60 from the proximal end 34 of Y-adaptor 32 and open the Y-adaptor lumen 38. The second catheter 12 is then moved distally over the guide wire 60 up through the Y-adaptor 32 and the guide catheter 22 until the balloon 20 of second catheter 12 is across the stenosis (at which point the valve 45 is re-closed to seal shut the Y-adaptor lumen 38 and guide catheter lumen 23). Finally, the balloon 20 is inflated to dilate the stenosis thereby re-establishing an acceptable blood flow (once the catheter 12 is removed from the treated arterial branch).

A variation of the first exchange sleeve is shown in FIGS. 2D and 2E. At its distal end, an exchange sleeve 80a has a connector clip 90 with a pair of opposed prongs 92, and each prong 92 has a distal end 94. As before, the sleeve 80a preferably has a length approximately the same as the length of the guide wire lumen 66, although exchange sleeve 80a can be appreciably longer than or even shorter than the length of guide wire lumen 66. The prongs 92 are an extension of a distal end 84a of the exchange sleeve 80a, and are resiliently flexible such that distal ends 94 may be pulled away from each other yet return to the position shown in FIGS. 2D and 2E. The exchange sleeve 80a also has a longitudinal slit 86a similar to longitudinal slit 86 (FIG. 2E). The connector clip 90 (including prongs 92) is preferably made of a polyethylene material thick enough to provide sufficient rigidity for accomplishing the functions described hereafter, yet flexible enough to permit selected separation of the distal ends 94 of the prongs 92. Although "prongs" are shown and described, it is contemplated that other means (such as threaded connections, friction-based couplers, magnets, etc.) for detachably securing the exchange sleeve to the Y-adaptor are possible.

To exchange catheters using the connector clip 90 version of exchange sleeve 80a, the catheter 12 is withdrawn proximally over guide wire 60 (which is held in a fixed position) in the manner previously described until the proximal end 68 of guide wire lumen 66 is at the proximal end 34 of Y-adaptor 32. The sealing valve 45 is once again closed to seal shut Y-adaptor lumen 38 and hold the catheter 12 and guide wire 60 in a fixed position relative to Y-adaptor 32. At this point the exchange sleeve 80a with clip 90 is mounted over both the guide wire 60 and catheter 12, by the lateral insertion method as previously described. With the guide wire 60 being held at 71, the sleeve 80a with clip 90 is moved distally until the distal ends 94 of clip 90 are adjacent the grasping point 71 (FIG. 2B). Next, the guide wire 60 is grasped at 87 proximally of the proximal end 82 of sleeve 80 and the guide wire 60 is released from grasping point 71. With the guide wire 60 still being held at 87, the clip 90 of sleeve 80 is moved distally until the distal ends 94 at clip 90 about the proximal end 34 of Y-adaptor 32.

The physician then slips the prongs 92 over the valve 45 (as sleeve 80a is moved distally) and positions distal ends 94 on the outer wall of Y-adaptor 32 distally of the valve 45 (as seen in FIG. 2D), thus removably attaching or securing the sleeve 80a (with clip 90) onto the Y-adaptor 32. Next, the guide wire is regrasped at 87a (FIG. 2D) instead of grasp point 87 (FIG. 2B). With sleeve 80a secured by clip 90, the catheter 12 is grasped at grasp point 88a (FIG. 2D) and pulled proximally over guide wire 60 through Y-adaptor lumen 38 and sleeve 80a while the guide wire 60 is held at grasp point 87a in a fixed position longitudinally relative to the Y-adaptor 32.

Next, the physician places fingers around the prongs 92 to grip and move knob 46 of valve 45 to reopen the sealing valve 45 thereby releasing guide wire 60 from the Y-adaptor 32 and likewise opening Y-adaptor lumen 38. The catheter 12 is then withdrawn until the proximal end 68 of guide wire lumen 66 is proximal to the proximal end 82 of sleeve 80a and the distal end 16 of catheter 12 is proximal to the proximal end 34 of Y-adaptor 32 (like shown in FIG. 2C). Next, the sealing valve 45 is closed to clamp the guide wire 60 in a fixed position within the proximal end 34 of the Y-adaptor 32 and seal shut the proximal end 34 of Y-adaptor lumen 38. The guide wire 60 is then released at 87a and the catheter 12 completely removed from guide wire 60 as previously described (for sleeve 80 without clip 90). The sleeve 80a with clip 90 from the Y-adaptor 32 may be removed along with catheter 12 by unclipping clip 90 and moving the sleeve 80a proximally with catheter 12. A second catheter 12 may be loaded on guide wire 60 and advanced to the stenosis for treatment in the manner previously described.

B. A Second Exchange Sleeve of the Present Invention

In another preferred embodiment, seen in FIGS. 3A–3D, a second exchange sleeve 100 of the present invention has a proximal end 102 and a distal end 104. The sleeve is preferably made of a stainless steel hypotube, such as 304 stainless steel. A longitudinal slit 106 is formed in a wall of the sleeve 100 extending from the proximal end 102 to the distal end 104. A protective lubricous coating of polymer material, such as strips of polyethylene or a Teflon coating, is disposed about the sides of the slit 106. The sleeve 100 has an inner lumen with a diameter that can be sized so that it is sufficient to encompass only the guide wire 60 and not the catheter 12. The second exchange sleeve 100 preferably has a length approximately the same as the length of guide wire lumen 66, although the exchange sleeve 100 can be appreciably longer than or even shorter than the length of guide wire lumen 66.

To exchange catheters using the second exchange sleeve 100, the physician first opens the sealing valve 45. Then the catheter 12 is withdrawn proximally over the guide wire 60 while the guide wire 60 is held in position longitudinally relative to the Y-adaptor 32 by grasping the guide wire 60 proximally of the proximal end 34 of Y-adaptor 32 at the grasping point 107 as seen in FIG. 3A. While so holding guide wire 60, the catheter 12 is then withdrawn until the proximal end 68 of guide wire lumen 66 is at the proximal end 34 of Y-adaptor 32, as previously described for the method using first exchange sleeve 80.

At this point or at some time earlier in the procedure, while still holding guide wire 60, the second sleeve 100 is mounted onto the guide wire 60 either by longitudinally or laterally loading onto the guide wire (the sleeve 100 is loaded over guide wire 60 only and not over the catheter 12). Once mounted over the guide wire 60, the distal end 104 of second sleeve 100 is positioned just proximal to the proximal end 68 of guide wire lumen 66 and the proximal end 34 of Y-adaptor 32 at 107. Next, the guide wire 60 is grasped proximally of the proximal end 102 of sleeve 100 as at 110 (FIG. 3B) and then released at 107. The catheter 12 is then grasped proximal to the proximal end 68 of guide wire lumen 66 (at 108) and withdrawn proximally over the guide wire 60 out of the Y-adaptor lumen 38. During this step, the sleeve 100 is grasped at its proximal end 102 in the same grasping movement as for guide wire 60 at grasp point 110 so that the sleeve 100 is held along with guide wire 60, or the sleeve 100 may be constrained from proximal movement because its proximal end 102 abuts the fingers grasping guide wire 60 at grasp point 110.

As the catheter 12 is withdrawn proximally, the proximal end 68 of guide wire lumen 66 passes alongside of the sleeve 100, thereby pulling (or forcing) the guide wire 60 laterally out of the lumen of sleeve 100 through the slit 106 therein in a progressive manner (see FIG. 3C). Accordingly, the second sleeve 100 is peeled off of the guide wire 60 as the catheter 12 is moved proximally. The lubricous material on the sides of slit 106 prevents scraping or damaging the protective lubricous coating of the guide wire 60 during this peeling phase. As seen in FIG. 3C at 111, during this peel away phase, the guide wire 60 extends through the second sleeve 100 to a point just proximal to the proximal end 68 of guide wire lumen 66 where the guide wire 60 exits sleeve 100 through the slit 106. By constraining the guide wire 60 in this manner, the guide wire 60 position can be maintained across the stenosis because the sleeve 100 prevents bowing or buckling of the guide wire 60 by providing lateral support thereto as the catheter 12 is withdrawn proximally over the guide wire 60.

The catheter 12 is withdrawn from the Y-adaptor 32 until the distal end 70 of the guide wire lumen 66 (distal end 16 of catheter 12, if the same) is proximal to the proximal end 34 of the Y-adaptor 32. At this point (see FIG. 3D), the second sleeve 100 is completely peeled off the guide wire 60 and the distal end 16 of catheter 12 is out of the Y-adaptor 32. Next, the sealing valve 45 is closed to seal shut the proximal end 34 of Y-adaptor lumen 38 and clamp the guide wire 60 into a fixed position longitudinally relative to the Y-adaptor 32, thereby maintaining the position of the guide wire 60 across the stenosis. The physician may then release the grasp of guide wire 60 at the grasp point 110. The catheter 12 is then further withdrawn proximally until the catheter 12 is fully removed from the guide wire 60. A second catheter 12 is loaded onto the guide wire 60 and maneuvered to the stenosis for treatment thereof in the manner previously described in the method of using first exchange sleeve 80.

A wire-only sleeve such as that seen in FIGS. 3B, 3C, and 3D may also be employed as an aid in withdrawing an over-the-wire catheter leaving a guide wire lumen extending the full length of the catheter from a guide catheter. In this instance, a long guide wire or guide wire extension is used and the sleeve is placed over the exposed guide wire proximally of the guide catheter. The sleeve is then peeled laterally off of the guide wire as the catheter is withdrawn proximally over the guide wire. Although the guide wire and such an over-the-wire catheter never assume a side-by-side relation, the sleeve prevents the guide wire from bowing laterally proximally of the catheter as the catheter is withdrawn.

C. An Exchange Coil of The Present Invention

In another preferred embodiment of the present invention, as seen in FIGS. 4A–4E, an elongate exchange coil 112 has a proximal end 114 and a distal end 116. As shown in FIG. 4A, the exchange coil 112 is shown in a compressed close-wound configuration positioned distally of the proximal end 14 of catheter 12. The exchange coil 112 has a pair of end tabs, with a first tab 118 mounted on the distal end 116 of coil 112 and a second tab 120 mounted on the proximal end 114 of coil 112. The exchange coil 112 has an inner lumen with a diameter sufficient to encompass both the guide wire 60 and the catheter 12.

To exchange catheters using exchange coil 112, the sealing valve 45 is re-opened and the catheter 12 is then withdrawn in the manner previously described (for the method using first exchange sleeve 80). In this case the guide wire 60 is grasped proximally at grasp point 122 as seen in FIG. 4A and catheter 12 pulled over guide wire 60 until the proximal end 68 of guide wire lumen 66 is just proximal the proximal end 34 of Y-adaptor 32 (see FIG. 4B). At some time earlier in the procedure, or in manufacture of catheter, the proximal end 114 of coil 112 is loaded over the distal end 16 of catheter 12 so that the coil 112 encompasses catheter 12 and is positioned adjacent the proximal end 14 of catheter 12 as seen in FIG. 4A. Thus, in the catheter removal procedure, the coil 112 is moved distally over the catheter 12 until coil 112 is proximally adjacent the proximal end 62 of guide wire 60. While still holding the guide wire 60 at 122, the distal end 116 of coil 112 is loaded over the proximal end 62 of guide wire 60 so that the coil 112 encompasses both the catheter 12 and guide wire 60 (see FIG. 4B).

The exchange coil 112 is then moved distally over both the catheter 12 and guide wire 60 until the distal end 116 of the exchange coil 112 is at some distance proximal (e.g., about 35 cm) to the proximal end 34 of the Y-adaptor 32 as seen in FIG. 4B. Next, the physician grasps the guide wire 60 at grasp point 124 to hold the guide wire 60 in position across the stenosis and the guide wire 60 is released at the grasp point 122 (see FIG. 4B).

The second tab 120 at the proximal end 114 of coil 112 is then grasped along with the guide wire 60 at grasping point 124 and both the proximal end 114 of coil 112 and guide wire 60 are restrained from axial movement relative to each other and from longitudinal movement relative to the Y-adaptor 32. While holding the guide wire 60 and second tab 120 so fixed, the first tab 118 at the distal end of coil 112 is grasped and pulled distally over the catheter 12 and guide wire 60 thereby stretching coil 112 until the distal end 116 of coil 112 is just proximal to the proximal end 34 of Y-adaptor 32 and just distal to the proximal end 68 of the guide wire lumen 66 (see FIG. 4C). At this point the elongate coil 112 in its expanded state is preferably approximately the same length as the guide wire lumen 66 although the exchange coil 112 obviously can be manipulated to vary its length relative to the length of the guide wire lumen 66.

The exchange coil 112 may be of two types. First, the exchange coil 112 may be an elastic type spring in which the coil 112, once elongated to an expanded state, is biased to return to its original compressed state (see FIG. 4D). This type of exchange coil 112 is preferably made of a spring steel. Second, the exchange coil 112 may be of a type such that the exchange coil 112 once elongated to an expanded state, is deformed and remains in that state (see FIG. 4E) such that coil 112 is selectively maintainable in a desired degree of elongation yet could be later re-compressed if so desired. This type of exchange coil 112 is preferably made of a soft, annealed stainless steel, such as annealed 304 stainless steel.

If the exchange coil 112 is the elastic type, then to remove the guide wire lumen 66 from Y-adaptor 32 over guide wire 60, the catheter 12 is grasped along with the grasping of first tab 118 of coil 112 at a point adjacent the distal end 70 of guide wire lumen 66 of catheter 12 (at 126 in FIG. 4C). With the first tab 18 and catheter 12 so grasped and the second tab 120 and guide wire 60 still being held at 124, the distal end 116 of coil 112 and the distal end 70 of guide wire lumen 66 are then moved proximally toward the fixed proximal end 114 of coil 112 (at 124) over guide wire 60 by allowing the exchange coil 112 to recompress. The catheter 12 is moved proximally until the distal end 16 of the catheter 12 (or distal end 70 of guide wire lumen 66) is proximal to the proximal end 34 of the Y-adaptor 32 and the proximal end 68 of guide wire lumen 66 is proximal to the proximal end 114 of coil 112 at grasp point 124 as seen in FIG. 4D. Similar to the previously described methods of catheter exchange using sleeves 80 and 100, the exchange coil 112 prevents the guide wire 60 from moving laterally away from the longitudinal axis of the catheter 12 as catheter 12 is pulled off of the guide wire 60. Thus the exchange coil 112, in addition to helping move the catheter 12, prevents the previously described guide wire buckling and bowing and the detrimental effects thereof that would occur in the absence of using the exchange coil 112.

If the nonelastic type exchange coil 112 is used, then the exchange coil 112 is elongated from the position shown in FIG. 4B to the position shown in FIG. 4C in the manner previously described. Thereafter, during the catheter exchange the exchange coil 112 remains in this expanded state. The guide wire 60 and proximal end 114 of coil 112 are still grasped at grasp point 124, thereby holding the coil 112 and guide wire 60 in a fixed position longitudinally relative to the Y-adaptor 32 so that the distal end 116 of coil 112 abuts or is adjacent to the proximal end 34 of Y-adaptor 32. Next, while holding the guide wire 60 and coil 112 so fixed, the catheter 12 is grasped at grasp point 128 (see FIG. 4C) and pulled proximally over the guide wire 60 and through the nonelastic coil 112 until the distal end 16 of catheter 12 is proximal to the proximal end 34 of Y-adaptor 32 and the proximal end 68 of guide wire lumen 66 is proximal to the proximal end 114 of coil 112 at grasp point 124 as seen in FIG. 4E. Like the elastic type coil, the expanded type coil 112 constrains the guide wire 60 from lateral movement during the withdrawal of catheter 12 through the coil 112, alleviating the detrimental results of withdrawing the catheter 12 with an unconstrained guide wire 60.

Hereafter, the steps of the exchange are the same for both types of the exchange coil 112. Once the distal end 16 of catheter 12 is proximal to the proximal end 34 of the Y-adaptor 32 (as shown in FIG. 4D and 4E), the sealing valve 45 is closed to seal shut the proximal end 34 at Y-adaptor 32 and clamp guide wire 60 into a fixed position longitudinally relative to the Y-adaptor 32. After releasing the grasped guide wire 60 at grasp point 124, the catheter 12 is further withdrawn proximally off the guide wire 60 until the catheter 12 is completely removed from the guide wire 60. During this final catheter withdrawal step, the exchange coil 112 may be removed from catheter 12 or may be retained by grasping the coil 112 at its distal end 116 along with the guide wire 60 at grasp point at 126 while the catheter 12 is withdrawn. A second catheter 12 is then loaded over the proximal end 62 of the guide wire 60 and maneuvered to the stenosis for dilating thereof in the manner previously described for the introduction of second catheters. The coil 112 may be slid proximally over the second catheter 12 (just after installation) to the proximal end 14 of catheter 12.

CONCLUSION

The constraining means of the present invention facilitates the removal of single operator exchange style catheters from a guide wire during a catheter exchange while maintaining the guide wire position across the stenosis so that the arterial pathway need not be re-established upon the introduction of a second catheter. The constraining or supporting means provides lateral support to the guide wire during the withdrawal of a single operator exchange style catheter lumen from a guide catheter lumen (or Y-adaptor) such that the danger of kinking, bowing or buckling of the guide wire, or even of the guide wire becoming dislodged from the stenotic area, is greatly reduced. In addition, the exchange constraining means of the present invention save many steps in the catheter exchange process that were required when the guide wire lumen had to be inched proximally out of the Y-adaptor so that the guide wire position could be maintained across the stenosis. The constraining means of the present invention may be used for any single operator exchange-type catheter and not just for a balloon dilatation single operator exchange style catheter.

Although the present invention has been described with reference to preferred embodiments, workers skilled in the art will recognize that changes may be made in form and detail without departing from the spirit and scope of the invention.

What is claimed is:

1. In a catheter system having a guide catheter, a catheter and a guide wire, wherein the catheter includes a guide wire lumen in a distal portion of the catheter with a length of the guide wire lumen being shorter than a length of the catheter, and wherein the guide wire extends through the guide wire lumen and extends with the catheter through a lumen in the guide catheter, a method for withdrawing the catheter from the guide catheter lumen while leaving the guide wire in position through the guide catheter lumen, the method comprising:

providing constraining means positioned proximal to the guide catheter lumen and substantially encompassing the guide wire for preventing the guide wire from bowing and significantly moving laterally away from the catheter;

holding the guide wire proximally adjacent the constraining means to prevent the guide wire from moving longitudinally relative to the guide catheter lumen;

withdrawing the catheter from the guide catheter lumen in a proximal, axial direction until a distal end of the guide wire lumen is proximal of the guide catheter lumen;

holding the guide wire at a point distal of the guide wire lumen to prevent the guide wire from moving longitudinally relative to the guide catheter lumen;

releasing the guide wire proximally adjacent the constraining means; and withdrawing the catheter in the proximal, axial direction until the guide wire lumen is free from the guide wire.

2. The method of claim 1 wherein the step of providing constraining means further comprises:

providing an elongated sleeve as the constraining means.

3. The method of claim 2 wherein the step of providing a sleeve further comprises:

providing an elongate slit in the sleeve extending from a proximal end of the sleeve to a distal end of the sleeve.

4. The method of claim 3 wherein the step of providing a sleeve comprises:

providing the sleeve with an inner diameter sized to encompass only the guide wire therein.

5. The method of claim 4 wherein the step of providing a sleeve further comprises:

loading the sleeve over a proximal end of the guide wire and therealong until the sleeve is positioned adjacent the proximal end of the guide catheter lumen.

6. The method of claim 5 wherein the first withdrawing step comprises:

forcing the guide wire to be pulled through the slit of the sleeve allowing the sleeve to be peeled off of the guide wire.

7. The method of claim 4 wherein the step of providing the sleeve further comprises:

inserting the guide wire longitudinally into the sleeve.

8. The method of claim 7 wherein the first withdrawing step comprises:

forcing the guide wire to be pulled through the slit of the sleeve allowing the sleeve to be pulled off of the guide wire.

9. The method of claim 2 wherein the step of providing a sleeve comprises:

providing the sleeve with an inner lumen with a diameter large enough to encompass both the guide wire and the catheter.

10. The method of claim 9 wherein the step of providing a sleeve further comprises:

inserting the guide wire and the catheter laterally into the sleeve through a longitudinal slit formed in the sleeve.

11. The method of claim 9 wherein the step of providing the sleeve further comprises:

loading the sleeve over a proximal end of the guide wire and catheter and therealong until the sleeve is positioned adjacent the proximal end of the guide catheter lumen.

12. The method of claim 2 wherein the step of providing a sleeve comprises:

forming the sleeve having a length slightly greater than a length of the guide wire lumen.

13. The method of claim 2 wherein the step of providing a sleeve comprises:

forming the sleeve having a length slightly shorter than a length of the guide wire lumen.

14. The method of claim 2 wherein the second withdrawing step comprises:

removing the sleeve with the catheter.

15. The method of claim 1 wherein the step of providing constraining means comprises:

forming the constraining means from an elongate coil.

16. The method of claim 15 wherein the step of providing constrainment means comprises:

moving the coil from a compressed state in which the coil is in a close-wound configuration encompassing a proximal end of the catheter to an expanded state in which the coil is elongated to a length slightly greater than the length of the guide wire lumen and positioned adjacent the proximal end of the guide catheter lumen encompassing both the catheter and the guide wire.

17. The method of claim 16 wherein the first withdrawing step comprises:
restraining a proximal end of the coil and the guide wire from longitudinal movement relative to the guide catheter lumen;
grasping a distal end of the expanded coil and the catheter proximal to the guide catheter lumen; and
moving the distal end of the coil and the catheter proximally toward the proximal end of the coil and recompressing the coil until the distal end of the guide wire lumen exits the guide catheter lumen and the coil returns to a compressed state.

18. The method of claim 16 wherein the first withdrawing step comprises:
forming the elongated coil so that it selectively maintains itself in an expanded state;
holding a proximal end of the expanded coil so that a distal end of the expanded coil is positioned proximally adjacent the proximal end of the guide catheter lumen; and
moving the catheter through the expanded coil toward the proximal end of the expanded coil until the distal end of the guide wire lumen exits the guide catheter lumen.

19. The method of claim 1 wherein the catheter system further comprises:
a proximal fitting having a proximal end and a distal end with a lumen extending therebetween, the distal end being rotatably mounted to a proximal end of the guide catheter, the proximal lumen being in fluid communication with the guide catheter lumen so that the guide wire and catheter extend through both the guide catheter lumen and proximal fitting lumen.

20. The method of claim 19 wherein the step of providing a sleeve comprises:
removably attaching a distal end of the sleeve to a proximal end of the guide catheter.

21. The method of claim 19 wherein the step of providing constraining means comprises:
positioning the constraining means proximal to the proximal fitting lumen.

22. The method of claim 21 wherein the first withdrawing step further comprises:
withdrawing the catheter from both the guide catheter lumen and the proximal fitting lumen until the distal end of the guide wire lumen is proximal to the proximal fitting lumen 23. The method of claim 19 wherein the proximal fitting has means for closing the proximal fitting lumen, and wherein the second holding step comprises:
actuating the closing means to limit longitudinal movement of the guide wire extending through the proximal fitting lumen relative to the guide catheter.

24. The method of claim 1 wherein the catheter is a dilatation balloon catheter.

25. The method of claim i wherein the guide wire lumen extends through a dilatation balloon located at a distal end of the catheter.

26. A catheter system comprising:
a guide catheter having a guide catheter lumen, a proximal end, and a distal end;
a catheter extending through the guide catheter lumen, the catheter having a guide wire lumen at a distal portion of the catheter with a proximal end and a distal end, wherein a length of the guide wire lumen is shorter than a length of the catheter;
a guide wire extending through the guide wire lumen and the guide catheter lumen; and
supporting means over a segment of the guide wire extending proximally from the guide catheter lumen for preventing bowing of the guide wire by maintaining that segment of the guide wire in close lateral proximity to the catheter as the catheter is withdrawn proximally from the guide catheter lumen and the guide wire is restrained from such proximal movement.

27. The apparatus of claim 26 wherein the supporting means comprises a sleeve with a longitudinal slit extending from a proximal end of the sleeve to a distal end of the sleeve.

28. The apparatus of claim 26 wherein the supporting means comprises a sleeve with an inner lumen with a diameter large enough to encompass both the guide wire and the guide wire lumen of the catheter.

29. The apparatus of claim 26 wherein the supporting means comprises a sleeve with an inner lumen with a diameter sized to encompass only the guide wire therein.

30. The apparatus of claim 26 wherein the supporting means comprises a elongate coil.

31. The apparatus of claim 30 wherein the coil has a first compressed state wherein the coil is in a closewound configuration and is positioned about the dilatation catheter adjacent a proximal end of the dilatation catheter and has a second expanded state wherein the coil is elongated to a length slightly greater than the length of the guide wire lumen and is positioned adjacent the proximal end of the guide catheter lumen about both the dilatation catheter and the guide wire.

32. The apparatus of claim 31 wherein the coil is selectively maintainable in its second expanded state.

33. The apparatus of claim 31 wherein the coil is biased towards its first compressed state.

34. The apparatus of claim 26 wherein the catheter system further comprises:
a proximal fitting having a proximal end and a distal end with a lumen extending therebetween, the distal end being connected to a proximal end of the guide catheter, the proximal fitting being in fluid communication with the guide catheter lumen so that the guide wire and catheter extend through both the guide catheter lumen and proximal fitting lumen.

35. The apparatus of claim 34 wherein the supporting means is positioned over a segment of the guide wire extending proximally from the proximal fitting lumen.

36. The apparatus of claim 34 wherein the proximal fitting has means for securing the guide wire from longitudinal movement relative to the proximal fitting lumen.

37. The apparatus of claim 34 wherein the supporting means comprises means for connecting the supporting means to the proximal end of the proximal fitting lumen, the connecting means having means for permitting clasping of the guide wire distal to the supporting means once the catheter has exited the proximal fitting lumen.

38. The apparatus of claim 26 wherein the supporting means has a length slightly greater than a length of the guide wire lumen.

39. The apparatus of claim 26 wherein the catheter is a dilatation balloon catheter.

40. The apparatus of claim 26 wherein the guide wire lumen extends through a dilation balloon located at a distal end of the catheter.

41. An apparatus for use with an intralumenal catheter system which has a guide wire and a catheter that has a guide wire lumen therein for slidably receiving the guide wire, both of which extend longitudinally through a guide lumen extending through both a guide catheter wherein the apparatus is adapted to maintain the guide wire in a desired position relative to the guide lumen during withdrawal of the catheter from the guide lumen, the apparatus comprising:

an elongated sleeve positioned generally adjacent a proximal end of the guide catheter and surrounding a segment of the guide wire, with the sleeve having an inner lumen which is suitable for providing lateral support to the guide wire during proximal withdrawal of the catheter from the guide lumen.

42. The apparatus of claim 41 wherein the sleeve includes a longitudinal slit from a proximal end of the sleeve to a distal end of the sleeve.

43. The apparatus of claim 41 wherein the inner lumen of the sleeve is large enough to encompass both the guide wire and the catheter.

44. The apparatus of claim 41 wherein the inner lumen of the sleeve is sized to encompass only the guide wire.

45. The apparatus of claim 41 wherein the sleeve comprises an exchange coil.

46. The apparatus of claim 45 wherein the exchange coil has a first compressed state wherein the coil is in a close-wound configuration and is positioned about a proximal end of the catheter about the dilatation catheter and has a second expanded state wherein the coil is elongated to a length slightly greater than the length of the guide wire lumen and is positioned adjacent the proximal end of the guide catheter about both the catheter and the guide wire.

47. The apparatus of claim 46 wherein the exchange coil is selectively maintainable in its second expanded state.

48. The apparatus of claim 46 wherein the exchange coil is biased towards its first compressed state.

49. The apparatus of claim 41 wherein the sleeve has a length slightly greater than a length of the guide wire lumen.

50. The apparatus of claim 41 wherein the sleeve has a length slightly shorter than a length of the guide wire lumen.

51. The apparatus of claim 41 wherein the catheter is a dilatation balloon catheter.

52. The apparatus of claim 41 wherein the guide wire lumen extends through a dilatation balloon located at a distal end of the catheter.

* * * * *

UNITED STATES PATENT AND TRADEMARK OFFICE
CERTIFICATE OF CORRECTION

PATENT NO. : 5,255,690

DATED : October 26, 1993

INVENTOR(S) : PETER T. KEITH, THOMAS V. RESSEMANN

It is certified that error appears in the above-identified patent and that said Letters Patent is hereby corrected as shown below:

Col. 19, line 55 after "lumen", insert --.--

Col. 19, line 65 delete "claim i", insert --claim 1--

Signed and Sealed this

Ninth Day of May, 1995

Attest:

BRUCE LEHMAN

*Attesting Officer*  *Commissioner of Patents and Trademarks*